(12) United States Patent
Chen et al.

(10) Patent No.: US 11,185,566 B2
(45) Date of Patent: Nov. 30, 2021

(54) TOTAL FLAVONOID EXTRACT FROM GYNURA FORMOSANA KITAM., PREPARATION METHOD THEREOF, AND USE OF SAME IN PREPARING DRUG OR HEALTH PRODUCT RELATED TO ALCOHOLIC FATTY LIVER DISEASE

(71) Applicant: ZHANGZHOU PIEN TZE HUANG PHARMACEUTICAL CO., LTD., Fujian (CN)

(72) Inventors: Zhiliang Chen, Fujian (CN); Jinming Huang, Fujian (CN); Fei Hong, Fujian (CN); Juan Yu, Fujian (CN); Zhiyi Luo, Fujian (CN); Xuxin Li, Fujian (CN)

(73) Assignee: Zhangzhou Pien Tze Huang Pharmaceutical Co., Ltd., Fujian (CN)

( * ) Notice: Subject to any disclaimer, the term of this patent is extended or adjusted under 35 U.S.C. 154(b) by 0 days.

(21) Appl. No.: 16/821,306

(22) Filed: Mar. 17, 2020

(65) Prior Publication Data

US 2020/0215140 A1 Jul. 9, 2020

Related U.S. Application Data

(63) Continuation of application No. PCT/CN2018/101164, filed on Aug. 17, 2018.

(30) Foreign Application Priority Data

Sep. 18, 2017 (CN) .......................... 201710840987.1

(51) Int. Cl.
   *A61K 36/00* (2006.01)
   *A61K 36/28* (2006.01)
   *A23L 33/105* (2016.01)
   *A61P 1/16* (2006.01)
   *A61K 31/7048* (2006.01)

(52) U.S. Cl.
   CPC ............ *A61K 36/28* (2013.01); *A23L 33/105* (2016.08); *A61K 31/7048* (2013.01); *A61P 1/16* (2018.01); *A61K 2236/333* (2013.01); *A61K 2236/51* (2013.01); *A61K 2236/53* (2013.01)

(58) Field of Classification Search
   CPC ..................................................... A61K 36/00
   USPC ......................................................... 424/725
   See application file for complete search history.

(56) References Cited

FOREIGN PATENT DOCUMENTS

| CN | 101100683 A | 1/2008 |
|---|---|---|
| CN | 102228534 A | 11/2011 |
| CN | 104151380 A | 11/2014 |
| CN | 107582587 A | 1/2018 |

OTHER PUBLICATIONS

English Translation of the Third Office Action, dated Dec. 23, 2020, Chinese Application No. 2017108409871.
Office Action dated Dec. 23, 2020 from Chinese Application No. 2017108409871.
Decision of Refusal of corresponding CN application CN2017108409871.
English Translation of Decision of Refusal of corresponding CN application CN2017108409871.
International Search Report, International Application No. PCT/CN2018/101164.
Written Opinion dated Nov. 2018, Application No. PCT/CN2018/101164.
English Translation of the First Office Action, dated Mar. 30, 2020, Application No. 2017108409871.
Chen, C., Establishment of Zebra Fish Model of Alcoholic Fatty Liver and Study on Liver Protection Effect of Gynura formosana Kitam., Medicine and Health Sciences in Chinese Master's Theses, No. 3, (2017) (English translation).
Yao, L., et al., "Research Process of Chemical Constituents and Biological Activities of the Genus *Gynura* Plants," Journal of Northern Horticulture, No. 24, (2016) (English translation).
Li, S., Compartive Study on the Effects of Six Dendrobium Polysaccharides on Alcoholic Liver injury, Section I of Engineering Science and Technology in Full Library Database of China's outstanding master degree thesis, No. 4, p. B024-28, (2014).
Luo, Y., "Introduction to Food Biotechnology," China Agricultural University Press, pp. 325-326 (Aug. 31, 2016).
Zhang, R., "Practical Ophthalmic Pharmacology," People's Military Medical Press, p. 388, Sep. 30, 2015.
Fend, D.L., et al., "Research on Extraction Technology of Flavonoids from Gynura divaricate (L.) DC.," Fujian Vocational College of Agriculture, Fujian Province 350007).
Chi, Z., "Identification and Diagnosis of Gastrointestinal and Hepatopancreatobiliary Diseases," Military Medical Science Press, pp. 578 (Nov. 30, 2003).
English Translation of the Second Office Action, dated Aug. 24, 2020, in corresponding Chinese Application No. 2017108409871.

*Primary Examiner* — Michael V Meller
(74) *Attorney, Agent, or Firm* — Elmore Patent Law Group, P.C.; Joseph Zucchero; Carolyn Elmore (57) ABSTRACT

A total flavonoid extract from *Gynura formosana* Kitam., comprising, in weight percent, 80-85% of rutin. A method for preparing the total flavonoid extract from *Gynura formosana* Kitam. comprises solvent extraction, complex enzymatic hydrolysis, and separation and purification by a macroporous resin. The total flavonoid extract from *Gynura formosana* Kitam. is used to prepare a drug or health product related to alcoholic fatty liver disease.

12 Claims, 3 Drawing Sheets

TOTAL FLAVONOID EXTRACT FROM GYNURA FORMOSANA KITAM., PREPARATION METHOD THEREOF, AND USE OF SAME IN PREPARING DRUG OR HEALTH PRODUCT RELATED TO ALCOHOLIC FATTY LIVER DISEASE

CROSS-REFERENCE TO RELATED APPLICATIONS

This application is a continuation application of International Patent Application No. PCT/CN2018/101164 with an international filing date of Aug. 17, 2018, designating the United States, and further claims priority benefits to Chinese Patent Application No. 201710840987.1, filed on Sep. 18, 2017. The contents of all of the aforementioned applications are incorporated herein by reference.

TECHNICAL FIELD

The present invention belongs to the field of medicines or health products, and particularly relates to a total flavonoid extract from *Gynura formosana* Kitam., and preparation method thereof, and use of same for treating alcoholic fatty liver disease.

BACKGROUND OF THE INVENTION

Alcoholic fatty liver disease (AFLD) refers to hepatic steatosis disease due to long-time excess alcohol consumption. AFLD is one of the clinically most common alcoholic liver diseases (ALD) and accounts for 90% of alcoholic liver diseases. A pathological feature of AFLD is that lipid accumulation in hepatocytes exceeds 5% of liver wet weight. In China, alcoholic liver disease has become the second common liver disease that leads to liver injury, after the most common viral liver diseases. Alcoholic liver disease would further progress into irreversible liver injury such as hepatic fibrosis and even cirrhosis which seriously threaten human life and health. Although there are big breakthroughs in modern medical study of pathogenesis of AFLD, there are no effective drugs for treating AFLD. The treatment for AFLD mainly includes abstinence and nutritional support, the effects of which are not satisfactory.

*Gynura formosana* Kitam. also called Bai Bei Tian Kui and Pien Tze Huang grass, is a herbaceous perennial plant of the genus Gynura Cass. nom. Cons. in the composite family. *Gynura formosana* Kitam. contains rich vitamins, alkaloids and flavonoid substances, and can be used for both medicine and food. Studies show that *Gynura formosana* Kitam. is mainly used for the treatment of diseases such as pneumonia, lung cancer, hepatitis, liver cirrhosis, hypertension and the like, and also has the effects of clearing away heat and toxic materials.

It is reported that the extract from *Gynura formosana* Kitam. can provide protection against alcoholic liver injury, and has the effect of protecting liver. Since the extract from *Gynura formosana* Kitam. contains a wide variety of chemical components, it is however not clear which chemical component is an active ingredient for the protection against alcoholic liver injury.

Therefore, further study is needed to investigate the active ingredients for providing protection against alcoholic liver injury in the extract from *Gynura formosana* Kitam., which has important significance for developing novel medicine for treating alcoholic fatty liver disease.

SUMMARY OF THE INVENTION

The goal of the present invention is to provide a total flavonoid extract from *Gynura formosana* Kitam., and further provide a preparation method thereof and use of same.

The goal of the present invention is realized by the following technical solutions:

In a first aspect, the present invention provides a total flavonoid extract from *Gynura formosana* Kitam., comprising, in weight percent, 80-85% of rutin.

In a second aspect, the present invention also provides a preparation method of the total flavonoid extract from *Gynura formosana* Kitam., comprising the steps of:

(1) Extraction: extracting *Gynura formosana* Kitam., with an extraction solvent to obtain an extraction solution, and adjusting the extraction solution to a pH of 4-8 to obtain a reaction solution;

(2) Enzymolysis: adding a complex enzyme into the reaction solution to carry out enzymolysis through a forced circular reaction at a temperature of 30° C. to 50° C. for 1 to 4 hours, then carrying out suction filtration, and collecting a filtrate;

(3) Extraction and concentration: extracting the filtrate by using a macroporous resin A to obtain an extracted solution, and concentrating the extracted solution to obtain a concentrated solution;

(4) Separation and purification: centrifuging the concentrated solution, collecting a supernatant and carrying out elution by using a macroporous resin B, measuring absorbance at a wavelength of 510 nm, collecting eluate, concentrating and drying the eluate to obtain an extract.

Preferably, in the above preparation method, the complex enzyme used in the enzymolysis step consists of papain, cellulase and pectinase.

Preferably, in the above preparation method, a weight ratio of the complex enzyme to the *Gynura formosana* Kitam. is 1:5 to 1:3.

Preferably, in the above preparation method, a weight ratio of papain to cellulase to pectinase in the complex enzyme is (0.5-1.5): (2-5): (1-3).

Preferably, in the above preparation method, the weight ratio of papain to cellulase to pectinase in the complex enzyme is 1:3:2.

Preferably, in the above preparation method, the macroporous resin A is one or more selected from the group consisting of AB-8, DM-130, HZ841, ZH-00, ZH-01, ZH-02, ZH-03, CAD-40, CAD-45 and BS-30; and the macroporous resin B is one or more selected from the group consisting of D-101, D-140, D-141, XAD-3, XAD-4, HP-20, HP-21, LD-605 and LSA-10.

Preferably, in the above preparation method, the extraction solvent in the extraction step is water, and a weight ratio of *Gynura formosana* Kitam. to water is 1: (20-60).

Preferably, in the above preparation method, in the separation and purification step, an ethanol aqueous solution with a volume concentration of 70-80% is adopted as an elution solvent, and the elution is performed at a rate of 3-15 m/h.

Preferably, in the above preparation method, in the separation and purification step, an ethanol aqueous solution with a volume concentration of 75% is adopted as an elution solvent, and the elution is performed at a rate of 5 m/h.

Preferably, in the above preparation method, the concentrated solution comprises total flavonoid from *Gynura formosana* Kitam. at a concentration of 0.5 mg/mL.

Preferably, in the above preparation method, the extraction and concentration step comprises: placing the filtrate into an extraction tank containing a macroporous resin A, stirring at 30° C. for 6 to 24 hours at 80-150 rpm, then filtering to obtain an absorbed macroporous resin A, adding ethanol solution having a volume concentration of 70-95% to the absorbed macroporous resin A, wherein the ethanol solution is added in an amount 10 to 30 times the weight of the absorbed macroporous resin A, followed by stirring at 30° C. for 6 to 24 hours at 80-150 rpm, and filtering to obtain an extracted solution.

Preferably, in the above preparation method, said adjusting the extraction solution to a pH of 4-8 is carried out with a hydrochloric acid or sodium hydroxide.

Preferably, in the above preparation method, said drying refers to freeze drying.

In a further aspect, the present invention provides a total flavonoid extract from *Gynura formosana* Kitam. prepared by the above preparation method.

In a further aspect, the present invention provides a pharmaceutical preparation, comprising the above mentioned total flavonoid extract from *Gynura formosana* Kitam. or a total flavonoid extract from *Gynura formosana* Kitam. prepared by the above preparation method as an active ingredient, wherein the active ingredient is mixed with a conventional auxiliary material and prepared according to a conventional process into clinically acceptable forms selected from the group consisting of tablets, capsules, powders, mixtures, pills, granules, syrups, plasters, suppositories, aerosols, ointments and injections.

The conventional auxiliary material can be selected from the group consisting of fillers, disintegrants, lubricants, suspending agents, adhesives, sweeteners, flavoring agents, preservatives, matrix and the like. Fillers include starch, pre-gelatinized starch, lactose, mannitol, chitin, microcrystalline cellulose, sucrose, and the like. Disintegrants include starch, pre-gelatinized starch, microcrystalline cellulose, sodium carboxymethyl starch, cross-linked polyvinylpyrrolidone, low substituted hydroxypropyl cellulose, croscarmellose sodium, and the like. Lubricants include magnesium stearate, sodium dodecyl sulfate, talcum powder, silicon dioxide and the like. Suspending agents include polyvinylpyrrolidone, microcrystalline cellulose, sucrose, agar, hydroxypropyl methyl cellulose and the like. Adhesives include starch slurry, polyvinylpyrrolidone, hydroxypropyl methyl cellulose and the like. Sweeteners include sodium saccharin, aspartame, sucrose, sodium cyclamate, glycyrrhetinic acid and the like. Flavoring agents include a sweetener and various essences. Preservatives include paraben, benzoic acid, sodium benzoate, sorbic acid and salts thereof, benzalkonium bromide, chloroethyl acetate, eucalyptus oil and the like. The matrix comprises PEG 6000, PEG 4000, insect wax and the like.

In a further aspect, the present invention provides use of the above mentioned total flavonoid extract from *Gynura formosana* Kitam. or a total flavonoid extract from *Gynura formosana* Kitam. prepared by the above preparation method or the above mentioned pharmaceutical preparation in preparing drug or health product for treating alcoholic fatty liver disease.

The technical solutions of the present invention have the following advantages:

(1) Through deep research on extract of *Gynura formosana* Kitam., a total flavonoid extract comprising 80-85% of rutin is extracted and separated from *Gynura formosana* Kitam. in the present invention. Further, pharmacodynamic experiment is carried out using alcoholic fatty liver disease zebra fish model. Experiment results show that the prepared total flavonoid extract from *Gynura formosana* Kitam. can provide effective protection against alcoholic liver injury and is effective in protecting liver, so can be used as a potential medicine for treating alcoholic liver injury.

(2) In the present preparation method of the total flavonoid extract from *Gynura formosana* Kitam., a unique complex enzyme which comprises specific enzymes at specific ratio is adopted for carrying out enzymolysis at 30° C. to 50° C. after the extraction step, so that the structure of the total flavonoid extract is prevented from being damaged at high temperatures, and the total flavonoid compounds can be extracted out to the maximum extent. Further, extraction and concentration with a macroporous resin A and separation and purification with a macroporous resin B are carried out, so that the extraction rate of the total flavonoid compounds of the *Gynura formosana* Kitam. can reach 1.8-2.0%, which is 30% or more higher compared with the extraction rate of the total flavonoid compounds by the existing method. The HPLC purity of rutin in the prepared total flavonoid extract can reach 80-85%.

BRIEF DESCRIPTION OF THE DRAWINGS

The present invention is described in detail with reference to examples and accompanying drawings, wherein.

DETAILED DESCRIPTION OF THE EMBODIMENTS

*Gynura formosana* Kitam. used in the following examples and experimental example of the present invention are taken from Dengke village, Longwen disctrict, Zhangzhou city, Fujian Province, and are identified as the *Gynura formosana* Kitam.

EXAMPLE 1

Figure 1:
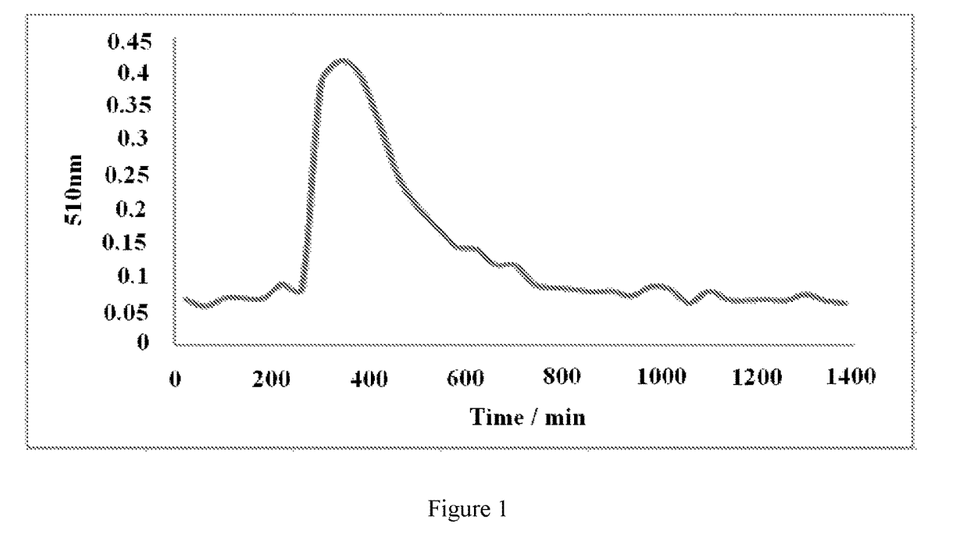
FIG. 1 shows an elution curve in Example 1 of the present invention.

A total flavonoid extract from *Gynura formosana* Kitam. is prepared according to the following method:

(1) Extraction: 100 g *Gynura formosana* Kitam. was added into water with a weight 30 times the weight of *Gynura formosana* Kitam. to carry out extraction, producing an extraction solution, which was then adjusted with a diluted hydrochloric acid to a pH of 5, obtaining a reaction solution;

(2) Enzymolysis: 25 g of complex enzyme consisting of papain, cellulase and pectinase with a weight ratio of 1: 3: 2 was added into the reaction solution to carry out enzymolysis through a forced circular reaction at 40° C. for 3 hours, and the resulted solution was suction filtered and a filtrate was collected;

(3) Extraction and Concentration: The filtrate was added to an extraction tank containing AB-8 macroporous resin and stirred for 12 hours at 30° C. and 100 rpm, then filtered to obtain an absorbed AB-8 macroporous resin. An ethanol solution with a volume concentration of 75% was added to the absorbed AB-8 macroporous resin at an amount 20 times the weight of the absorbed AB-8 macroporous resin, then stirred for 12 hours at 30° C. and 120 rpm and then filtered to obtain an extracted solution. The extracted solution was vacuum concentrated to produce a concentrated solution which comprises a total flavonoid extract from *Gynura formosana* Kitam. at a concentration of 0.5 mg/mL;

(4) Separation and Purification: The concentrated solution was centrifuged at 10,000 rpm for 10 minutes, and a supernatant was collected and placed into a chromatographic column filled with a macroporous resin D-101 for stationary adsorption for 60 min. Then the column was eluted with an aqueous solution of ethanol with a volume concentration of 75% at a rate of 5 m/h, and absorbance was measured at a wavelength of 510 nm. An elution curve was plotted with absorbance as Y-axis versus elution time as X-axis, as shown in FIG. 1. Eluate corresponding to the absorption peak area of the elution curve was collected, concentrated, and freeze-dried to obtain the total flavonoid extract from *Gynura formosana* Kitam.

Through calculation, the extraction rate of the total flavonoid extract from *Gynura formosana* Kitam. is 2.0%.

By referring to FIG. 1, the elution curve of the eluate shows a significant single absorption peak at 340 min, indicating the relatively pure flavonoid in the eluate.

A. The total flavonoid extract from *Gynura formosana* Kitam. was identified with an infrared spectrum according to the following method:

The method comprises the following steps: A certain amount of dried rutin standard was mixed with dried potassium bromide at a weight ratio of 1: 100, ground and prepared into a solid pellet. The pellet was then tested with a Fourier infrared spectrophotometer within a scanning range of 4000 $cm^{-1}$ to 400 $cm^{-1}$, a resolution of 4 and a scanning number of 4, thereby obtaining an infrared spectrum. The total flavonoid extract from *Gynura formosana* Kitam. was tested in the same manner to obtain an infrared spectrum. The results are shown in FIG. 2.

Figure 2:
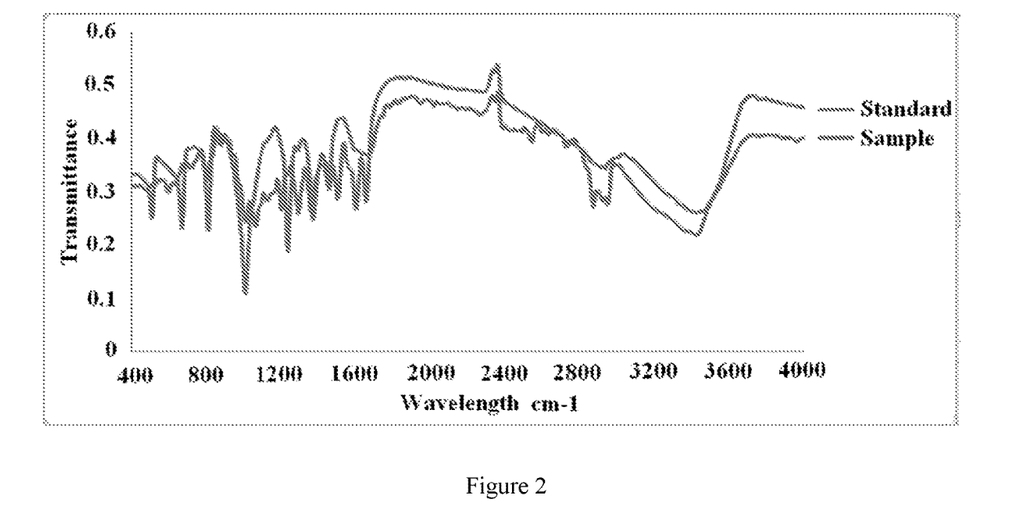
FIG. 2 shows an infrared spectrum of a total flavonoid extract from *Gynura formosana* Kitam. prepared in Example 1 of the present invention.

By referring to FIG. 2, both the infrared spectrums of the rutin standard and the total flavonoid extract from *Gynura formosana* Kitam. show a wide and strong absorption peak around 3685.455 $cm^{-1}$ to 3018.177 $cm^{-1}$, corresponding to telescopic vibration peak of-OH, indicating there are large amount of phenolic hydroxyl groups or sugar hydroxyl groups. A weak absorption peak occurs at 2914.036 $cm^{-1}$, corresponding to a telescopic vibration peak of a carbon-hydrogen bond, indicating less hydrogen on saturated carbon. A strong peak appears at 1654.694 $cm^{-1}$ in each spectrum, corresponding to a telescopic vibration of C=O. The peaks in the two spectrums appear at substantially same position and have substantially same shape, indicating that the extract is a flavonoid. Bending vibration peak of hydroxyl groups appears at 1371.88 $cm^{-1}$ and 1362.89 $cm^{-1}$. An absorption peak caused by ortho hydrogens of phenyl ring appears at 804.80 $cm^{-1}$ and 810.56 $cm^{-1}$. An absorption peak caused by the position of a substituent on the phenyl ring appears at 1010.07 $cm^{-1}$ to 696.62 $cm^{-1}$, but the peak position is different in the two spectrums, indicating the hydroxyl substitution position of the extract is different from that of the rutin standard. These results indicate that the extract contains hydroxyl, carbonyl, and other functional groups such as different position-substituted benzene rings, and the characteristic absorption peaks are substantially consistent. Thus, it can be determined that the extract is a flavonoid compound.

B. The total flavonoid extract from *Gynura formosana* Kitam. was analyzed by liquid chromatography to determine the content of rutin therein according to the following method:

B1. Liquid Chromatography Conditions

Liquid Chromatography Conditions are as follows:

Eclipse XDB-C18 AnalyticalGuard Column (4.6×12.5 mm, 5 μm) and ZOR BZX Eclipse XDB-C18 Column (4.6×150 mm, 5 μm) were used as a protection column. Flow rate is 0.5 mL/min; Column temperature is 35° C. Detection wavelength is 368 nm, 254 nm and 210 nm, respectively; Sample loading volume is 10 μL; Mobile phases consists of (A) 0.03% formic acid aqueous solution and (B) Acetonitrile; Gradient elution procedures are as follows: 0-10 min, 80% (A) and 20% (B); 10-12 min, 76% to 80% (A) and 20% to 24% (B); 12-20 min, 76% (A) and 24% (B); 20-25 min, 70% to 76% (A) and 24% to 30% (B); 25-48 min, 70% (A) and 30% (B).

B2. Preparation of Control Sample Solution 0.001 g Rutin was weighed accurately and dissolved in 1 mL of methanol to prepare a single control sample solution of 1 mg/mL. The control sample solution was filtered with a disposable filter and then loaded into a small test tube for later use.

B3. Determination

The control sample solution and a test sample solution (1 μg/μL methanol solution of the total flavonoid extract prepared in Example 1) are respectively accurately sucked and injected to the liquid chromatography column to perform analysis according to the above mentioned liquid chromatography conditions.

Figure 3:
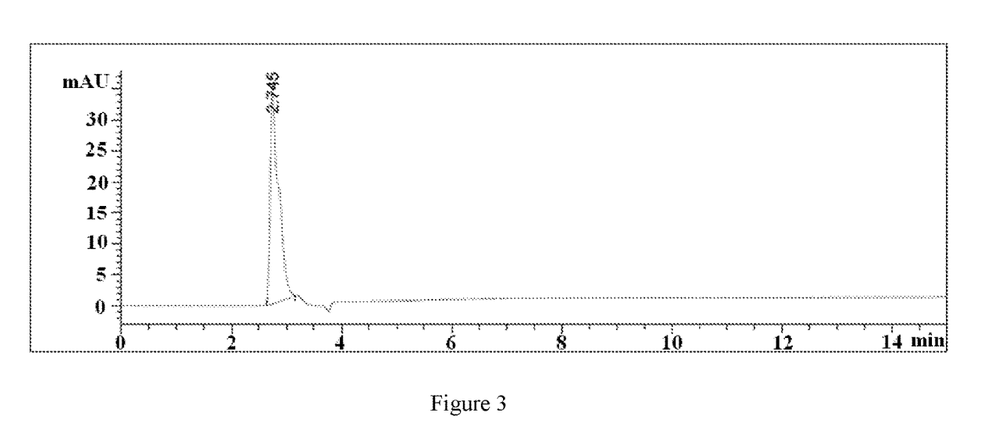
FIG. 3 shows a HPLC chromatogram of a rutin control solution in Example 1 of the present invention.
Figure 4:
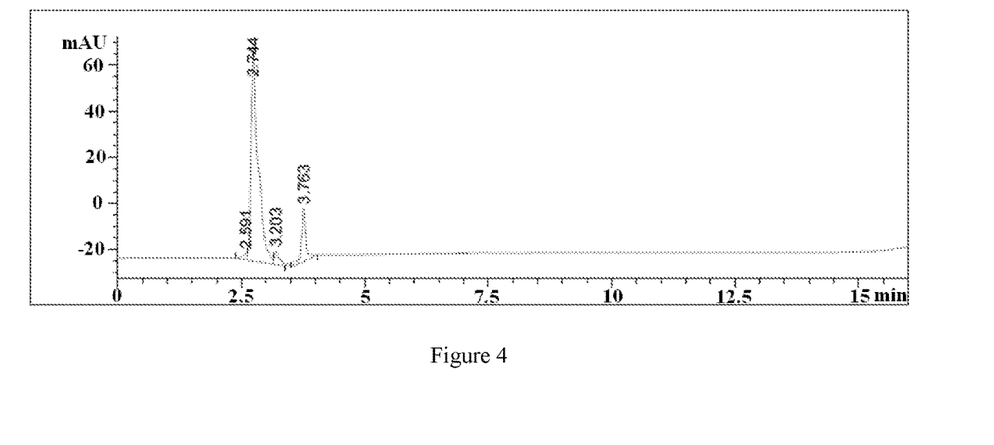
FIG. 4 shows an HPLC chromatogram of the total flavonoid extract from *Gynura formosana* Kitam. prepared in Example 1 of the present invention.

The HPLC chromatogram of the control sample solution is shown in FIG. 3, and the HPLC chromatogram of the test sample solution is shown in FIG. 4.

By referring to FIG. 3, the rutin control solution can be completely isolated within 10 minutes. A substantially straight baseline is observed in the chromatogram of Rutin under the chromatographic conditions of this experiment, and peak tailing is not observed. There are no interfering peaks of impurities. The peaks appear earlier and the retention time is 2.745 min.

By referring to FIG. 4, the amount of rutin in the extract was 81.29% as calculated by area normalization.

EXAMPLE 2

A total flavonoid extract from *Gynura formosana* Kitam. is prepared according to the following method:

(1) Extraction: 100 g *Gynura formosana* Kitam. was added into water with a weight 20 times the weight of *Gynura formosana* Kitam. to carry out extraction, producing an extraction solution, which was then adjusted with diluted sodium hydroxide solution to a pH of 8, obtaining a reaction solution;

(2) Enzymolysis: 20 g of complex enzyme consisting of papain, cellulase and pectinase with a weight ratio of 0.5:5:1 was added into the reaction solution to carry out enzymolysis through a forced circular reaction at 30° C. for 4 hours, and the resulted solution was suction filtered and a filtrate was collected;

(3) Extraction and Concentration: The filtrate was added to an extraction tank containing DM-130 macroporous resin and stirred for 24 hours at 30° C. and 80 rpm, then filtered to obtain an absorbed DM-130 macroporous resin. An ethanol solution with a volume concentration of 95% was added to the absorbed DM-130 macroporous resin at an amount 10 times the weight of the absorbed DM-130 macroporous resin, then stirred for 24 hours at 30° C. and 80 rpm and then filtered to obtain an extracted solution. The extracted solution was vacuum concentrated to produce a concentrated solution which comprises a total flavonoid extract from *Gynura formosana* Kitam. at a concentration of 0.5 mg/mL;

(4) Separation and Purification: The concentrated solution was centrifuged at 6,000 rpm for 8 minutes, and a supernatant was collected and placed into a chromatographic column filled with a macroporous resin HP-21 for stationary adsorption for 60 min. Then the column was eluted with an aqueous solution of ethanol with a volume concentration of 80% at a rate of 3 m/h, and absorbance was measured at a wavelength of 510 nm. An elution curve was plotted with absorbance as Y-axis versus elution time as X-axis. Eluate corresponding to the absorption peak area of the elution curve was collected, concentrated, and freeze-dried to obtain the total flavonoid extract from *Gynura formosana* Kitam.

Through calculation, the extraction rate of the total flavonoid extract from *Gynura formosana* Kitam. is 1.82%.

The total flavonoid extract from *Gynura formosana* Kitam. was analyzed by liquid chromatography to determine the content of rutin therein according to the method as described in section B of example 1. According to the resulted HPLC chromatogram, the amount of rutin in the total flavonoid extract was 80% in this example.

EXAMPLE 3

A total flavonoid extract from *Gynura formosana* Kitam. is prepared according to the following method:

(1) Extraction: 100 g *Gynura formosana* Kitam. was added into water with a weight 60 times the weight of *Gynura formosana* Kitam. to carry out extraction, producing an extraction solution, which was then adjusted with a diluted hydrochloric acid to a pH of 4, obtaining a reaction solution;

(2) Enzymolysis: 32 g of complex enzyme consisting of papain, cellulase and pectinase with a weight ratio of 1.5:2:3 was added into the reaction solution to carry out enzymolysis through a forced circular reaction at 50° C. for 1 hour, and the resulted solution was suction filtered and a filtrate was collected;

(3) Extraction and Concentration: The filtrate was added to an extraction tank containing ZH-01 macroporous resin and stirred for 6 hours at 30° C. and 150 rpm, then filtered to obtain an absorbed ZH-01 macroporous resin. An ethanol solution with a volume concentration of 70% was added to the absorbed ZH-01 macroporous resin at an amount 30 times the weight of the absorbed ZH-01 macroporous resin, then stirred for 6 hours at 30° C. and 150 rpm and then filtered to obtain an extracted solution. The extracted solution was vacuum concentrated to produce a concentrated solution which comprises a total flavonoid extract from *Gynura formosana* Kitam. at a concentration of 0.5 mg/mL;

(4) Separation and Purification: The concentrated solution was centrifuged at 8,000 rpm for 5 minutes, and a supernatant was collected and placed into a chromatographic column filled with a macroporous resin XAD-3 for stationary adsorption for 60 min. Then the column was eluted with an aqueous solution of ethanol with a volume concentration of 70% at a rate of 15 m/h, and absorbance was measured at a wavelength of 510 nm. An elution curve was plotted with absorbance as Y-axis versus elution time as X-axis. Eluate corresponding to the absorption peak area of the elution curve was collected, concentrated, and freeze-dried to obtain the total flavonoid extract from *Gynura formosana* Kitam.

Through calculation, the extraction rate of the total flavonoid extract from *Gynura formosana* Kitam. is 1.91%.

The total flavonoid extract from *Gynura formosana* Kitam. was analyzed by liquid chromatography to determine the content of rutin therein according to the method as described in section B of example 1. According to the resulted HPLC chromatogram, the amount of rutin in the total flavonoid extract was 85% in this example.

Experiment Example 1

Experimental study of the total flavonoid extract from *Gynura formosana* Kitam. against zebra fish alcoholic fatty liver injury I Experimental Materials Digital Inverted Phase Contrast Microscope (IX 51, Japan Olympus); Nikon SMZ18 Digital Microscope; Fully Automatic Biochemical Analyzer (BS-220, Mindray Biomedical Electronics Co. Ltd., Shenzhen); Tissue Embedding Machine (BMJ-III, JOYWARE, Changzhou); Microtome (RM 2235, Leica, Germany); Water Bath-Slide Drier (PHY-III, JOYWARE, Changzhou); Microplate Reader (SUN-RISE, Tecan, Switzerland); Tissue Homogenizer (PRO200, PRO Scientific, US); High Speed Freeze Centrifuge (Centufuge 5810R, Eppendorf, Germany); Reverse Osmosis Pure Water System (RO-200, Shanghai Hitech Instruments Co., Ltd); MDA Assay Kit (Beyotime Biotechnology); SOD Assay Kit (Beyotime Biotechnology); Ethanol absolute (Xilong Scientific); Oil-Red O Stain (Aladdin); PBS Buffer Solution (Thermo-Fisher Scientific); Propylene Glycol (Xilong Scientific); Glycerin (Xilong Scientific); N-Phenmethylthiourea (Sigma); Tricaine methane sulfonic Acid (Sigma); Paraformaldehyde (Beijing Tuoyingfang Scientific Co., Ltd); Xylene (Xilong Scientific); Hematoxylin-eosin (HE). The above reagents are all analytically pure. The experimental kits are provided by Beyotime Biotechnology.

II Experimental Methods

1. Preparation of Test Drug

A total flavonoid extract from *Gynura formosana* Kitam. is prepared according to the method of the example 1 and used as a test drug.

2. Experimental Animal Feeding and Grouping

Wild-type adult zebra fish for use in the experiment were purchased from a flower bird market in Zhangzhou city, and were cultured in a constant-temperature environment of 28° C. The fish were exposed to laboratory illumination for 14 hours and dark for 10 hours alternatively controlled with an automatic timer for continuous seven days, during which the fish were daily fed with quantitative bait material at regular intervals.

Baby zebra fish for use in the experiment were obtained by laboratory culture of wild type TU zebra fish. The zebra fish were cultured according to the Westerfield method as follows: The fish were exposed to illumination for 14 hours and dark 10 hours alternately. Male and female were separately cultured, and were daily fed with fresh fairy shrimp at regular intervals. In the night before the experiment, the TU zebra fish with a male and female ratio of 1:1 were placed into a mating tank where the male and female were separated by a partition board inserted in the tank; Next morning the partition board was removed, and the fish mated to produce eggs. The eggs were collected and placed into a constant-temperature incubator for culture at 28° C. for 96 hours post-fertilization, during which water was refreshed at regular intervals and dead eggs were removed.

In order to determine the maximum non-lethal concentration of the total flavonoid extract from *Gynura formosana*

Kitam. for repairing the zebra fish alcoholic fatty liver injury, chronic toxicity tests for the zebra fish were carried out by a conventional method comprising the following steps: 60 adult zebra fish were randomly assigned to six groups, with 10 fish in each group. Each group was cultured in a separate tank. Five groups were cultured with 1.0% alcohol solution wherein the total flavonoid extract from *Gynura formosana* Kitam. was dissolved. The solution was refreshed daily and the culture lasted for seven continuous days. The remaining one group of zebra fish was cultured with normal water for use as a control group. After the experiment was started, the poisoning symptom and the death number of the fish were recorded every day, and dead fish were timely removed. The dose of each group is shown in Table 1.

TABLE 1

Groups in chronic toxicity test of the total flavonoid extract from *Gynura formosana* Kitam. for zebra fish

| Group | Number of fish | Drug Concentration (mg/mL) |
|---|---|---|
| 1 | 10 | 0 |
| 2 | 10 | 0.03 |
| 3 | 10 | 0.06 |
| 4 | 10 | 0.12 |
| 5 | 10 | 0.18 |
| Control Group | 10 | Normal water |

Note:
The control group was cultured with normal water, and other groups were cultured with 1.0% alcohol solution.

Acute toxicity test for the baby zebra fish was carried out according to the conventional method comprising the following steps: The baby zebra fish were randomly divided into seven groups, with 180 fish in each group. Each group was cultured in a separate tank. Six groups were cultured for continuous 32 hours with 2.0% alcohol solution wherein the total flavonoid extract from *Gynura formosana* Kitam. was dissolved. The remaining one group was cultured with normal water for use as a control group. After the experiment was started, the poisoning symptom and the death number of the fish were recorded every day, and dead fish were timely removed. The dose of each group is shown in Table 2.

Both the adult zebra fish and baby zebra fish were divided into a control group, a model group, and 5 groups of the total flavonoid extract with high, medium and low doses. The high, medium and low dose groups of adult zebra fish were cultured for continuous 28 days with 1.0% alcohol solution to which drug was added at corresponding concentration respectively, during which the culture solution was refreshed at regular intervals. The control group was cultured with normal water. The high, medium and low dose groups of baby zebra fish were cultured for 32 hours with 2.0% alcohol solution to which drug was added at corresponding concentration respectively, and the control group is cultured with normal water.

TABLE 2

Groups in acute toxicity test of the total flavonoid extract from *Gynura formosana* Kitam. for baby zebra fish

| Group | Number of fish | Drug Concentration (mg/mL) |
|---|---|---|
| 1 | 180 | 0 |
| 2 | 180 | 0.03 |
| 3 | 180 | 0.06 |
| 4 | 180 | 0.08 |

TABLE 2-continued

Groups in acute toxicity test of the total flavonoid extract from *Gynura formosana* Kitam. for baby zebra fish

| Group | Number of fish | Drug Concentration (mg/mL) |
|---|---|---|
| 5 | 180 | 0.10 |
| 6 | 180 | 0.12 |
| Control Group | 180 | Normal water |

Note:
The control group was cultured with normal water, and other groups were cultured with 2.0% alcohol solution.

3. Liver Index Determination for Adult Zebra Fish

Figure 5:
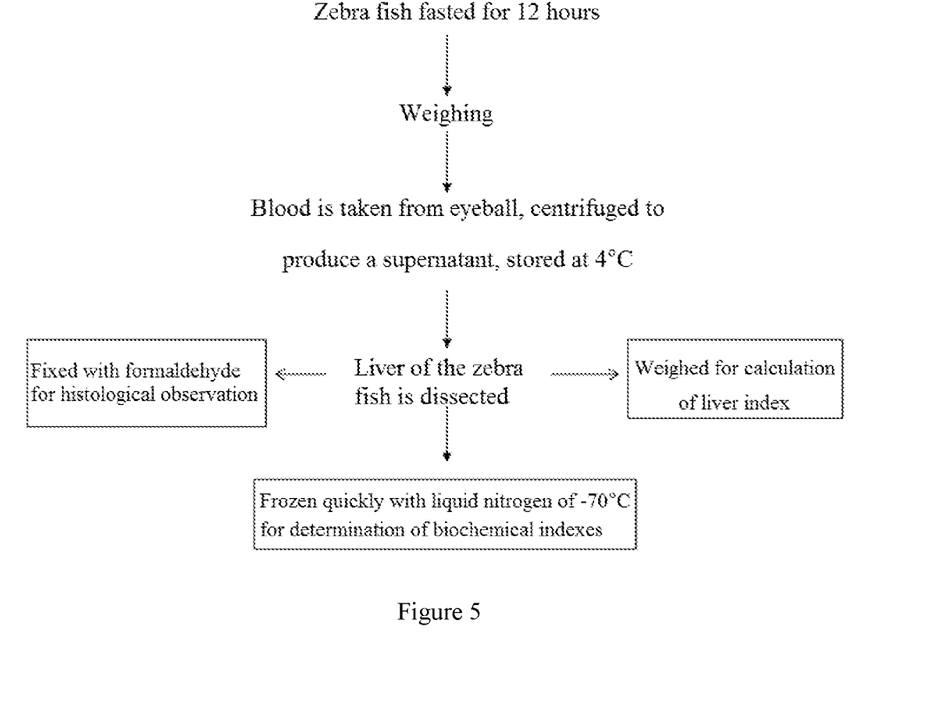
FIG. 5 shows a procedure for sacrificing zebra fish and collecting sample in experimental example 1 of the present invention.

The zebra fish in each experimental group fasted for 12 hours after the last refreshing of water, then weighed and sacrificed. Blood was taken from eyeball. 50 fish in total were selected from the control group, the model group and three groups of the experimental groups, with 10 fish in each group. The fish were sacrificed and weighed immediately after blood collection. Required liver tissues were quickly separated and weighed, and then fixed with formaldehyde or stored in liquid nitrogen. The procedure for sacrificing the zebra fish and collecting sample is shown in FIG. 5.

Calculation of the Liver Index was performed according to the following equation:

$$\text{Liver Index} = \frac{\text{Wet weight of liver (g)}}{\text{Body weight (g)}} \times 100\%$$

4. Detection of Serum Biochemical Indexes of Liver Function of Zebra Fish

Blood was centrifuged for 10 min at 4000 r/min and 4° C. A supernatant was collected and analyzed with a full-automatic biochemical analyzer to determine levels of serum aspartate transaminase (AST), alanine transaminase (ALT), total cholesterol (TC) and triglyceride (TG) according to instructions of the kit. The anti-oxidation index SOD and anti-stress index MDA in the liver were determined according to instructions of the kit.

5. He Staining of Liver of Adult Zebra Fish

The fixed tissue sample was dehydrated (dehydration sequence: 75% ethanol 30 min→90% ethanol 10 min→95% ethanol 10 min→95% ethanol 10 min→100% ethanol 10 min→100% ethanol 10 min→100% ethanol 10 min→xylene I 5 min→xylene II 5 min→xylene III 5 min.), embedded with paraffin, and cut into slides of 4 The slides were heated at 70° C. for 30 min, then stained with hematoxylin-eosin (HE), sealed with neutral gum, and observed under a microscopy.

6. Detection of Influence of the Total Flavonoid Extract from *Gynura formosana* Kitam. on Liver Biochemical Indexes of Baby Zebra Fish After the experiment is carried out for 32 hours, 50 fish were randomly selected from each of the control group, the model group and three groups treated with the extract at high, medium and low concentrations. A full-automatic biochemical analyzer was adopted to determine AST and ALT contents as well as SOD activity and MDA content in a homogenate of the baby zebra fish according to the instructions of the kit. Determination was repeated three times for each group. Data were recorded and analyzed.

7. Statistical Analysis

Experimental data were presented in the form of mean value±standard deviation ($\bar{x}$±s). The statistical analysis was carried out using Statistical Software SPSS10.0 and Single- Factor Variance Analysis. P values <0.05 were considered to demonstrate statistically significant difference, and P values <0.01 were considered to demonstrate very statistically significant difference.

III. Experimental Results

1. Determination of Maximum Non-lethal Concentration of the Total Flavonoid Extract from *Gynura formosana* Kitam. for Repairing the Zebra Fish Alcoholic Fatty Liver Injury The results of chronic toxicity tests and acute toxicity tests of the total flavonoid extract from *Gynura formosana* Kitam. for the adult zebra fish are shown in Table 3 and Table 4. As can be seen from Table 3 and Table 4, the adult zebra fish in each group exhibited normal appearance, traveling ability and mental states, and no death were observed after one week administration of the extract. For the baby zebra fish, within 32 hours administration of the extract, death were observed in the group treated with the total flavonoid extract of 0.08 mg/mL, and death were observed at 4 h in the group treated with the total flavonoid extract of 0.12 mg/mL, and the death rate is 7% at 32 h, but no large-scale death were observed. Therefore, the groups treated with the total flavonoid extract of 0.08 mg/mL, 0.04 mg/mL and 0.02 mg/mL were designed as the high, medium and low doses groups of the baby zebra fish.

TABLE 3

Results of the chronic toxicity test of the total flavonoid extract for the adult zebra fish

| Drug Concentration (mg/mL) | Number of fish | Number of Deaths | Number of Survival |
|---|---|---|---|
| 0 | 10 | 0 | 10 |
| 0.03 | 10 | 0 | 10 |
| 0.06 | 10 | 0 | 10 |
| 0.12 | 10 | 0 | 10 |
| 0.18 | 10 | 0 | 10 |
| Control Group | 10 | 0 | 10 |

(Note: The control group was cultured with normal water and other groups were cultured with 1.0% alcohol solutions, respectively)

TABLE 4

Results of the acute toxicity test of the total flavonoid extract for the adult zebra fish

| Drug Concentration (mg/mL) | Number of fish | Number of Deaths | Number of Survival |
|---|---|---|---|
| 0 | 180 | 0 | 180 |
| 0.03 | 180 | 0 | 180 |
| 0.06 | 180 | 0 | 180 |
| 0.08 | 180 | 1 | 179 |
| 0.10 | 180 | 6 | 174 |
| 0.12 | 180 | 13 | 167 |
| Control Group | 180 | 0 | 180 |

(Note: The control group was cultured with normal water and other groups were cultured with 2.0% alcohol solutions, respectively.)

2. Effect of the Total Flavonoid Extract from *Gynura formosana* Kitam. on Body Weight, Liver Weight and Liver Index of Adult Zebra Fish The effect of the total flavonoid extract from *Gynura formosana* Kitam. on body weight, liver weight and liver index of adult zebra fish is shown in Table 5. As can be seen from Table 5, compared with the control group, the adult zebra fish in the model group treated with alcohol exhibit reduced body weight, increased liver weight and increased liver index. The difference is statistically significant (P<0.05), indicating the alcohol has a toxic effect on the zebra fish to a certain extent, and leads to injury to the zebra fish liver. Compared with the model group, the zebra fish in the groups treated with the total flavonoid extract of different concentrations exhibit reduced liver weight, increased body weight and increased liver index, and the differences between the medium and high dose groups and the model group are statistically significant (P<0.05), which indicates that the total flavonoid extract is effective in improving the liver index of the zebra fish.

TABLE 5

Effect of the total flavonoid extract from *Gynura formosana* Kitam on body weight, liver weight and liver index of adult zebra fish with alcoholic liver ($\bar{x} \pm s$, n = 10)

| Group | Body Weight | Liver Weight | Liver Index (g/g) |
|---|---|---|---|
| Control group | 0.298 ± 0.03 | 0.0050 ± 0.0007 | 0.0170 ± 0.0011 * |
| Model group | 0.276 ± 0.02 | 0.0059 ± 0.0009 | 0.0212 ± 0.0014 |
| High dose group | 0.294 ± 0.04 | 0.0056 ± 0.0006 | 0.0175 ± 0.0015 * |
| Medium dose group | 0.283 ± 0.02 | 0.0055 ± 0.0006 | 0.0184 ± 0.0012 * |
| Low dose group | 0.285 ± 0.030 | 0.0054 ± 0.0007 | 0.0197 ± 0.0016 |

Note: Compared with model group, p * < 0.05.

3. Effect of the Total Flavonoid Extract from *Gynura formosana* Kitam. on the Serum Indexes of the Adult Zebra Fish with Alcoholic Fatty Liver Contents of aspartate transaminase (AST), alanine transaminase (ALT), total cholesterol (TC) and triglyceride (TG) in serum of the zebra fish are shown in Table 6.

As can be seen from Table 6, compared with the control group, the zebra fish in the model group exhibit significantly elevated serum AST and ALT activities (P<0.05), and obviously increased TG index, and the difference is very statistically significant (P<0.01), indicating culture with alcohol can obviously promote the formation of alcoholic fatty liver in zebra fish. The zebra fish in groups treated with different dose of the total flavonoid extract exhibit a descending trend in serum AST, ALT, TC and TG levels, wherein the differences in ALT, AST and TG are statistically significant compared with the model group (P<0.05), which indicates that the total flavonoid extract from *Gynura formosana* Kitam. has good effect in inhibiting the increase of serum ALT, AST and TG in the zebra fish body.

SOD activity and MDA levels in serum and liver of the zebra fish are shown in Table 7. As can be seen from Table 7, the zebra fish in the model group exhibit significantly reduced SOD activity (P<0.05) and significantly increased MDA content (P<0.05) compared with the control group, indicating that the alcohol has a toxic effect on the zebra fish liver and leads to decrease in anti-oxidation ability and oxidative stress level in the fish body. Compared with the model group, the zebra fish in different dose groups of the total flavonoid extract exhibit increased SOD activity, wherein the differences in the medium and high dose groups are statistically significant (P<0.05). Each dose group of the total flavonoid extract exhibits reduced MDA content in liver of the zebra fish. The results indicate that the total flavonoid extract from *Gynura formosana* Kitam. has a certain prevention and treatment effect on the alcoholic fatty liver of the zebra fish caused by alcohol.

TABLE 6

Effect of the total flavonoid extract from *Gynura formosana* Kitam. on ALT, AST, TC and TG in serum of zebra fish with alcoholic liver ($\bar{x} \pm s$, n = 10)

| Group | ALT (U/L) | AST (U/L) | TC (mmol/L) | TG (mmol/L) |
|---|---|---|---|---|
| Control group | 91.17 ± 24.45 * | 397.78 ± 21.45 * | 4.61 ± 0.27 | 1.25 ± 0.28 * * |
| Model group | 179.76 ± 16.45 | 547.35 ± 35.87 | 3.65 ± 0.40 | 2.90 ± 0.36 |
| High dose group | 115.94 ± 18.83 * | 423.88 ± 42.34 * | 4.43 ± 0.64 | 1.84 ± 0.33 * |
| Medium dose group | 126.12 ± 25.34 * | 445.25 ± 34.94 * | 4.21 ± 0.41 | 2.38 ± 0.37 |
| Low dose group | 156.29 ± 26.16 | 496.70 ± 48.55 | 3.70 ± 0.45 | 2.87 ± 0.48 |

Note:
Compared with alcohol model group, P * < 0.05, and P * * < 0.01.

TABLE 7

Effect of the total flavonoid extract from *Gynura formosana* Kitam. on SOD and MDA in serum and liver tissue of zebra fish with alcoholic liver ($\bar{x} \pm s$, n = 10)

| Group | SOD (U/mgprot) Serum | SOD (U/mgprot) Liver | MDA (nmol/mgprot) Serum | MDA (nmol/mgprot) Liver |
|---|---|---|---|---|
| Control group | 1.26 ± 0.32 * | 0.94 ± 0.17 | 9.15 ± 2.75 * | 8.58 ± 2.33 |
| Model group | 0.74 ± 0.25 | 0.60 ± 0.19 | 15.58 ± 2.45 | 14.16 ± 2.98 |
| High dose group | 1.16 ± 0.24 * | 0.89 ± 0.21 | 11.43 ± 2.05 | 13.39 ± 2.21 |
| Medium dose group | 1.07 ± 0.23 * | 0.81 ± 0.15 | 12.11 ± 3.10 | 11.82 ± 2.53 |
| Low dose group | 0.97 ± 0.30 | 0.77 ± 0.20 | 13.57 ± 2.94 | 12.09 ± 1.84 |

Note:
Compared with alcohol model group, P * < 0.05.

4. Effect of the Total Flavonoid Extract from *Gynura formosana* Kitam. on Biochemical Indexes Related to Liver of the Baby Zebra Fish The effect of the total flavonoid extract from *Gynura formosana* Kitam. on ALT, AST, SOD and MDA in a homogenate of the baby zebra fish with alcoholic liver is shown in Table 8.

As can be seen from Table 8, compared with the control group, baby zebra fish in the model group exhibit significant decrease in ALT, AST and SOD activities, and the difference is very statistically significant (P<0.01). MDA appeared to increase significantly, and the difference is very statistically significant (P<0.01). ALT and AST show different trend in their changes, because present ALT and AST activity were detected in homogenates of tissues while in previous studies ALT and AST activity were detected in serum. After liver injury in the model group, cell permeability is enhanced, and ALT and AST activities in serum are enhanced. However, when the whole body of the animal is considered, ALT and AST synthesis abilities of liver cell decreased after liver injury, so the total activities of ALT and AST decreased, illustrating the effect of alcohol on ALT and AST from different angles.

Each dose group of the total flavonoid extract from *Gynura formosana* Kitam. exhibit increase in the ALT, AST and SOD activities of the zebra fish with alcoholic liver, indicating that the total flavonoid extract is effective in protection of liver normal growth and development of the baby zebra fish or is effective in repairing liver injury, thereby reducing liver swelling and fatty droplets accumulation in the liver of the baby fish, and enhancing the ability of the liver cells to synthesize AST and ALT, so that the total vitality of the AST and ALT is improved.

ALT activity increase in the high-dose group of the total flavonoid extract reaches a very significant level (P<0.01), and ALT activity increase in the medium-dose group of the total flavonoid extract reaches a significant level (P<0.05). AST activity increase in the high-dose group and the medium-dose group of the total flavonoid extract reaches a significant level (P<0.05). Each dose group exhibits a certain increase in the SOD level while a certain decrease in the MDA level. The above results show that the total flavonoid extract from *Gynura formosana* Kitam. has a certain prevention and treatment effect on alcoholic fatty liver of the alcohol-induced baby zebra fish, and can reduce the degree of self-stress in the zebra fish body.

TABLE 8

Effects of the total flavonoid extract from *Gynura formosana* Kitam. on ALT, AST, SOD and MDA levels in homogenate of baby zebra fish with alcoholic liver ($\bar{x} \pm s$, n = 8)

| Group | ALT (U/L) | AST (U/L) | SOD (mmol/L) | MDA (mmol/L) |
|---|---|---|---|---|
| Control group | 66.54 ± 7.29 * * | 584.53 ± 25.67 * * | 80.01 ± 6.24 * * | 1.52 ± 0.46 * * |
| Model group | 33.49 ± 6.52 | 305.27 ± 21.41 | 46.62 ± 7.18 | 3.67 ± 0.60 |
| High dose group | 59.78 ± 5.21 * * | 474.92 ± 31.27 * | 61.53 ± 4.84 | 3.06 ± 0.17 |

TABLE 8-continued

Effects of the total flavonoid extract from *Gynura formosana* Kitam. on ALT, AST, SOD and MDA levels in homogenate of baby zebra fish with alcoholic liver ($\bar{x} \pm s$, n = 8)

| Group | ALT (U/L) | AST (U/L) | SOD (mmol/L) | MDA (mmol/L) |
|---|---|---|---|---|
| Medium dose group | 51.40 ± 8.29 * | 445.79 ± 26.46 * | 57.16 ± 5.95 | 2.89 ± 0.38 |
| Low dose group | 45.91 ± 7.89 | 402.36 ± 25.31 * | 58.38 ± 4.10 | 2.55 ± 0.40 * |

Note:
Compared with model group, P * < 0.05, and P * * < 0.01.

IV. Experimental Conclusions

A novel zebra fish alcoholic fatty liver model is adopted in the experiment in order to investigate whether the total flavonoid extract from *Gynura formosana* Kitam. has the effect of protecting liver. The model has the advantages of large sample quantity, simple experimental technique, short experiment period, low cost and the like.

Experimental results show that in the experiment for adult zebra fish, compared with model group, each dose group of the total flavonoid extract exhibits a certain decrease in the liver weight and the liver index, and also a decrease in AST, ALT, TC and TG content in serum of the zebra fish, thereby reducing liver cells injury in the zebra fish. The SOD activity level is improved, thereby enhancing the anti-oxidation ability of the zebra fish. The MDA content level is reduced, thereby reducing the oxidative stress level in the zebra fish body. The biochemical index of the baby zebra fish disclosed by the invention indicated that the total flavonoid extract from *Gynura formosana* Kitam. can improve the ALT, AST and SOD activities in the homogenate of the baby zebra fish body, thereby enhancing the ability of the liver cells to synthesize AST and ALT. The MDA content level is reduced, and among those groups the best effect is observed in the high-dose group (0.08 mg/mL) of the total flavonoid extract. The above experimental results show that the total flavonoid extract from *Gynura formosana* Kitam. can provide effective protection against alcoholic liver injury, and have the effects of protecting liver. The study of the total flavonoid extract from *Gynura formosana* Kitam. provides a pharmacodynamic research foundation for preparing drugs for treating alcoholic liver injury.

It is to be understood that the above-described examples are merely illustrative of the embodiments and are not intended to limit the embodiments. It will be apparent to one of ordinary skill in the art that other different forms of changes or variations can be made on the basis of the above description. It is to be understood that various changes or modifications may be made herein without departing from the scope of the invention as defined by the appended claims.

The invention claimed is:

1. A method of preparing an extract from *Gynura formosana* Kitam., the extract comprising, 80% wt.-85% wt. of rutin, the method comprising the steps of:
   (1) extracting *Gynura formosana* Kitam., with an extraction solvent to obtain an extraction solution, and adjusting the extraction solution to a pH of 4-8 to obtain a reaction solution;
   (2) adding an enzyme complex comprising papain, cellulose and pectinase into the reaction solution to carry out enzymolysis through a forced circular reaction at a temperature of 30° C. to 50° C. for 1 hour to 4 hours, then carrying out suction filtration, and collecting a filtrate;
   (3) extracting the filtrate with a macroporous resin A to obtain an extracted solution, and concentrating the extracted solution to obtain a concentrated solution; wherein the macroporous resin A is selected from the group consisting of AB-8, DM-130, HZ841, ZH-00, ZH-01, ZH-02, ZH-03, CAD-40, CAD-45, BS-30 and mixtures thereof;
   (4) centrifuging the concentrated solution, collecting a supernatant and carrying out elution by using a macroporous resin B, measuring absorbance at a wavelength of 510 nm, collecting the resulting eluate, concentrating and drying the eluate to obtain an extract from *Gynura formosana* Kitam; wherein the macroporous resin B is selected from the group consisting of D-101, D-140, D-141, XAD-3, XAD-4, HP-20, HP-21, LD-605, LSA-10 and mixtures thereof.

2. The method of claim 1, wherein a weight ratio of the enzyme complex to the *Gynura formosana* Kitam. is 1: 5 to 1: 3.

3. The method of claim 1, wherein a weight ratio of papain to cellulase to pectinase in the enzyme complex is (0.5-1.5): (2-5): (1-3).

4. The method of claim 3, wherein the weight ratio of papain to cellulase to pectinase in the enzyme complex is 1:3:2.

5. The method of claim 1, wherein in the extraction in step 1, the extraction solvent is water, and a weight ratio of *Gynura formosana* Kitam. to water is 1: (20-60).

6. The method of claim 1, wherein:
   in step 4, an ethanol aqueous solution with a volume concentration of 70-80% is adopted as an elution solvent, and the elution is performed at a rate of 3-15 m/h; and
   the concentrated solution comprises a total flavonoid from *Gynura formosana Kitam.* at a concentration of 0.5 mg/mL.

7. The method of claim 2, wherein a weight ratio of papain to cellulase to pectinase in the enzyme complex is (0.5-1.5): (2-5): (1-3).

8. The method of claim 7, wherein the weight ratio of papain to cellulase to pectinase in the enzyme complex is 1:3:2.

9. The method of claim 2, wherein in step 1, the extraction solvent is water, and a weight ratio of *Gynura formosana* Kitam. to water is 1: (20-60).

10. The method of claim 3, wherein in step 3, the extraction solvent is water, and a weight ratio of *Gynura formosana* Kitam. to water is 1: (20-60).

11. The method of claim 2, wherein:
    in step 4, an ethanol aqueous solution with a volume concentration of 70-80% is adopted as an elution solvent, and the elution is performed at a rate of 3-15 m/h; and the concentrated solution comprises total flavonoid from *Gynura formosana* Kitam. at a concentration of 0.5 mg/mL.

12. The method of claim 3, wherein:

in step 4, an ethanol aqueous solution with a volume concentration of 70-80% is adopted as an elution solvent, and the elution is performed at a rate of 3-15 m/h; and the concentrated solution comprises total flavonoid from *Gynura formosana* Kitam. at a concentration of 0.5 mg/mL.

\* \* \* \* \*